(12) United States Patent
Hegyi et al.

(10) Patent No.: US 6,251,409 B1
(45) Date of Patent: Jun. 26, 2001

(54) USE OF PARTICLES IN THE COMPOSITION OF COSMETIC PRODUCTS

(75) Inventors: Edit Hegyi; Susan Szathmary; Peter Grandics, all of Carlsbad, CA (US)

(73) Assignee: Clarigen, Inc., Carlsbad, CA (US)

( * ) Notice: Subject to any disclaimer, the term of this patent is extended or adjusted under 35 U.S.C. 154(b) by 0 days.

(21) Appl. No.: 09/188,569

(22) Filed: Nov. 10, 1998

Related U.S. Application Data

(60) Provisional application No. 60/065,193, filed on Nov. 11, 1997.

(51) Int. Cl.[7] .............................. A61K 7/00; A61K 7/021
(52) U.S. Cl. .............................................. 424/401; 424/63
(58) Field of Search .............................. 424/401, 63, 484, 424/485; 514/78.03, 937, 944

(56) References Cited

U.S. PATENT DOCUMENTS

| | | | |
|---|---|---|---|
| 1,205,883 | * | 11/1916 | Smith . |
| 5,961,990 | * | 10/1999 | Delrieu et al. ........................ 424/401 |

FOREIGN PATENT DOCUMENTS

| | | | |
|---|---|---|---|
| 0 363 921 | 4/1990 | (EP) | .............................. G01N/33/53 |
| 2 737 668 | 2/1997 | (FR) | .............................. B01J/2/06 |
| 1 205 883 | 9/1970 | (GB) | .............................. C08F/45/00 |

* cited by examiner

*Primary Examiner*—Thurman K. Page
*Assistant Examiner*—S. Howard
(74) *Attorney, Agent, or Firm*—Oppenheimer Wolff & Donnelly LLP

(57) ABSTRACT

The present invention provides a decorative cosmetic composition that is visually distinct comprising a translucent or transparent particle and a cosmetic base. In addition, the present invention provides a decorative cosmetic composition that has both a functional effect, such as for cleansing or massage, and a distinct visual effect.

27 Claims, No Drawings

USE OF PARTICLES IN THE COMPOSITION OF COSMETIC PRODUCTS

This application claims benefit of provisional application No. 60/065,193 Nov. 11, 1997.

FIELD OF THE INVENTION

The present invention is directed to compositions useful as perfumes, creams, moisturizers, lotions, oils, massage creams and other cosmetic uses.

BACKGROUND

In the cosmetic industry, there is a large emphasis on aesthetic attractiveness of products as well as on adaptation of the use of different physical, chemical, and biological effects to increase the efficacy of cosmetic treatment by given products. Some are so called built-in features of those products, for example, the use of liposomes to incorporate nourishing factors for the skin cells. This invention is related to both aspects of the aforementioned attractiveness: aesthetic and functional. The addition of particles to different cosmetic bases creates a distinctive visual effect, as well as adds to their function through the massaging, cleansing effects of the particles. Currently available cleansers with sand or other inorganic particles have an abrasive effect, which can be irritating. A certain number of people, therefore, cannot tolerate such products. At this point, to the best of our knowledge, there are no cosmetic products, which contain massaging, biofriendly, and non-abrasive particles in cosmetic bases.

SUMMARY OF THE INVENTION

The present invention provides compositions comprising particles and a base. Simple and efficient methods for producing such compositions are also described herein. With the addition of particles, which may be opaque, but preferably transparent or translucent, of different sizes and/or colors to cosmetic bases, a variety of applications can be produced. In one embodiment, the compositions comprise transparent or translucent beads and perfume or other transparent or translucent cosmetic material which produce a distinctive look. The use of colored particles and their different mixtures will further define these products. In a further embodiment, a transparent container and a transparent or translucent base material having suitable viscosity relative to the density of particles are used wherein the beads float or are suspended within the base material. The flotation of the particles provides additional visual effect. Alternatively, the particles' density relative to the base is such that with minimal agitation, the particles are easily dispersed throughout the base. In another preferred embodiment, the compositions comprise particles in a cosmetic base where the particles create a particular texture for the cosmetic material. Finally, the presence of the beads in cosmetics lend a massaging and cleansing effect to the product when applied directly to the skin. As used herein, it will be understood that the article "a", unless otherwise indicated, means singular or plural.

DETAILED DESCRIPTION OF THE INVENTION

The subject invention provides novel compositions, which provide cosmetic products with a distinct, novel look, as well as texture and feel. The invention comprises transparent or translucent colored beads of different sizes and a base, such as a perfume, cologne, or any type of cosmetic base, contained in, for example, creams, moisturizers, lotions, etc., such as oils, waxes, powder phases, filling phases, proteins, proteoglycans, other constituents of mineral and animal origin, and the like (see, for example, U.S. Pat. Nos. 5,443,855; 5,234,682; 4,973,473; 4,488,564; 4,636,524; 4,482,537; 3,766,267 and 4,416,873, incorporated herein by reference). For perfume and cologne compositions, virtually any kind of synthetically made and naturally occurring bead particles may be used, such as agarose, ceramic, silica, polymeric, cellulose, dextran, etc. In a preferred embodiment, the beads comprise agarose, preferably ClariBeads (available from Clarigen, Inc., 5922 Farnsworth Conn., Carlsbad, Calif. 92008).

For creams, moisturizers, lotions, and the like, where a cleansing and massaging effect is desired through direct contact with the skin, it is preferred that a biofriendly, biodegradable, non-abrasive particle is used, such as agarose, preferably ClariBeads.

The use of ClariBeads represents the best means of providing all the features described below: ClariBeads are biofriendly, made of agarose with a special cross-linking technology (described, for example, in U.S. Pat. No. 5,466,377, incorporated herein in its entirety), which lends them the necessary stability and elasticity. They are biodegradable by bacteria commonly found in our ecosystems. The low dry material content and low density of particles is a key element in order to achieve the floating or suspending effect in clear solutions, perfumes, etc. Particles of various sizes, as well as various colors, may be used for different applications. Although colored particles of virtually any size can be used to achieve the visual effect, colored particles ranging from about 300 to about 1500 $\mu$m is preferred and colored particles ranging from about 800 to about 1100 $\mu$m is more preferred. For a functional effect, such as cleansing, it is preferred that beads are used ranging from about 300 to about 1500 $\mu$m but more preferably in the range from about 300 to about 800 $\mu$m; or for massaging, beads of about 1500 $\mu$m and larger are preferred.

COLORING THE BEADS

Materials to be used include base beads (ClariBeads from Clarigen, Inc.), and a large variety of coloring materials such as Remazole Black B, Reactive Blue 2, Reactive Blue-Sepharose CL6B, Reactive Blue 4, 5, 15, Reactive Blue 72-agarose, Reactive Blue 114, 160, Reactive Brown 10, Reactive Brown 10-agarose, Reactive Green 5, Reactive Green 5-agarose, Reactive Green 19, Reactive Green 19-agarose, Reactive Orange 14, Reactive Red 2, 4, 120, Reactive Violet 5, Reactive Yellow 2, 3, 13, 81, 66, and any other dye having reactive groups suitable to interact with the particles.

Method: 100 g of 4% cross-linked agarose were suspended in 890 ml of water containing 10 g NaCl and 500 mg Cibacron blue dye. After 30 minutes of stirring, a solution of 200 mg NaOH in 20 ml water was added and mixing continued overnight. The resin was washed with copious amounts of water to remove excess dye and stored in water containing 0.02% sodium azide.

ADDING THE PARTICLES

It is a simple addition of the selected type of particles to the selected cosmetic base. The addition of beads result in a new texture, and a new look for traditional products. Technically, it creates a new product every time the beads are added. The addition and mixing procedure of the particles to the base product can be performed under a large variety of conditions in terms of temperature, pH, speed, etc., depending upon the base material selected.

We claim:

1. A decorative cosmetic composition comprising:
   a translucent or transparent agarose, ceramic, silica, cellulose, or dextran particle that is cross-linked; and
   a cosmetic base; wherein said base is transparent or translucent and together with said particle produces a visually distinct cosmetic composition.

2. The decorative cosmetic composition of claim 1, wherein said particle is agarose.

3. The decorative cosmetic composition of claim 1, wherein said particle is a colored particle.

4. The decorative cosmetic composition of claim 3, wherein said particle is colored with a dye having reactive groups suitable to interact with said particle.

5. The decorative cosmetic composition of claim 4, wherein said dye is selected from the group consisting of: Remazole Black B, Reactive Blue 2, Reactive Blue-Sepharose CL6B, Reactive Blue 4, Reactive Blue 5, Reactive Blue 15, Reactive Blue 72-agarose, Reactive Blue 114, Reactive Brown 10, Reactive Brown 10-agarose, Reactive Green 5, Reactive Green 5-agarose, Reactive Green 19, Reactive Green 19-agarose, Reactive Orange 14, Reactive Red 2, Reactive Red 4, Reactive Red 120, Reactive Violet 5, Reactive Yellow 2, Reactive Yellow 3, Reactive Yellow 13, Reactive Yellow 81 and Reactive Yellow 66.

6. The decorative cosmetic composition of claim 1, wherein said cosmetic base comprises perfume or cologne compositions.

7. The decorative cosmetic composition of claim 1, wherein said base comprises creams, moisturizers, lotions, oils, waxes, powder phases, filling phases, proteins, proteoglycans, or cosmetic constituents of mineral or animal origin.

8. The decorative cosmetic composition of claim 1, wherein the particle size ranges from about 300 to about 1500 µm.

9. The decorative cosmetic composition of claim 8 wherein the particle size ranges from about 800 to about 1100 µm.

10. The decorative cosmetic composition of claim 1, wherein said base has a suitable viscosity relative to the density of said particle such that said particle floats or is suspended within said cosmetic base forming a visually distinct decorative cosmetic composition.

11. The decorative cosmetic composition of claim 1, wherein said particle has a suitable density relative to said cosmetic base such that said particle is easily dispersed throughout said base with minimal agitation forming a visually distinct decorative cosmetic composition.

12. The decorative cosmetic composition of claim 1, wherein said particle within said base creates a decorative cosmetic composition having a particular texture.

13. A decorative cosmetic composition comprising:
    a translucent or transparent agarose, ceramic, silica, cellulose, or dextran particle that is cross-linked; and
    a cosmetic base; wherein said particle within said base creates a decorative cosmetic composition that has a functional effect and a distinct visual effect.

14. The decorative cosmetic composition of claim 13, wherein said particle is agarose.

15. The decorative cosmetic composition of claim 13, wherein said particle is a colored particle.

16. The decorative cosmetic composition of claim 15 wherein said particle is colored with a dye having reactive groups suitable to interact with said particle.

17. The decorative cosmetic composition of claim 16, wherein said dye is selected from the group consisting of: Remazole Black B, Reactive Blue 2, Reactive Blue-Sepharose CL6B, Reactive Blue 4, Reactive Blue 5, Reactive Blue 15, Reactive Blue 72-agarose, Reactive Blue 114, Reactive Brown 10, Reactive Brown 10-agarose, Reactive Green 5, Reactive Green 5-agarose, Reactive Green 19, Reactive Green 19-agarose, Reactive Orange 14, Reactive Red 2, Reactive Red 4, Reactive Red 120, Reactive Violet 5, Reactive Yellow 2, Reactive Yellow 3, Reactive Yellow 13, Reactive Yellow 81 and Reactive Yellow 66.

18. The decorative cosmetic composition of claim 13 wherein said base comprises creams, moisturizers, lotions, oils, waxes, powder phases, filling phases, proteins, proteoglycans, or cosmetic constituents of mineral or animal origin.

19. The decorative cosmetic composition of claim 13, wherein the functional effect is for massage.

20. The decorative cosmetic composition of claim 19, wherein the particle size is at least about 1500 µm.

21. The decorative cosmetic composition of claim 13, wherein the functional effect is for cleansing.

22. The decorative cosmetic composition of claim 21, wherein the particle size ranges from about 300 to about 1500 µm.

23. The decorative cosmetic composition of claim 22, wherein the particle size ranges from about 300 to about 800 µm.

24. The decorative cosmetic composition of claim 1 or 13, wherein said colored particle is the same color.

25. The decorative cosmetic composition of claim 1 or 13, wherein said colored particle is a mixture of different colors.

26. The decorative cosmetic composition of claim 1 or 13, wherein said particles are the same size.

27. The decorative cosmetic composition of claim 1 or 13, wherein said particles are a mixture of different sizes.

* * * * *